(12) United States Patent  (10) Patent No.: US 8,689,377 B2
Hannemann et al.  (45) Date of Patent: Apr. 8, 2014

(54) RADAR-EQUIPPED PATIENT BED FOR A MEDICAL IMAGING APPARATUS, AND OPERATING METHOD THEREFOR

(75) Inventors: Thilo Hannemann, Erlangen (DE); Stefan Popescu, Erlangen (DE); Georg Wittmann, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 253 days.

(21) Appl. No.: 12/780,046

(22) Filed: May 14, 2010

(65) Prior Publication Data

US 2010/0292559 A1  Nov. 18, 2010

(30) Foreign Application Priority Data

May 14, 2009  (DE) .......................... 10 2009 021 232

(51) Int. Cl.
 *A47B 13/00*  (2006.01)
 *A61B 5/05*  (2006.01)
(52) U.S. Cl.
 USPC ............... 5/601; 600/407; 600/425; 600/430; 600/534; 324/309; 324/318
(58) Field of Classification Search
 USPC .......... 600/301, 430, 407, 425, 534; 324/309, 324/318; 607/60; 5/601
 See application file for complete search history.

(56) References Cited

U.S. PATENT DOCUMENTS

| | | | |
|---|---|---|---|
| 5,606,259 A * | 2/1997 | Potthast et al. ............... | 324/318 |
| 6,023,166 A * | 2/2000 | Eydelman ..................... | 324/318 |
| 7,417,433 B2 * | 8/2008 | Heid et al. .................... | 324/318 |
| 2005/0073424 A1 | 4/2005 | Ruoss et al. | |
| 2005/0107693 A1 * | 5/2005 | Fear et al. ..................... | 600/430 |
| 2006/0173273 A1 | 8/2006 | Boese et al. | |
| 2007/0013376 A1 * | 1/2007 | Heid et al. .................... | 324/309 |
| 2007/0159332 A1 * | 7/2007 | Koblasz ..................... | 340/572.1 |
| 2007/0208235 A1 * | 9/2007 | Besson et al. ................. | 600/301 |
| 2008/0071169 A1 | 3/2008 | Craddock et al. | |
| 2009/0070939 A1 * | 3/2009 | Hann ............................ | 5/652.1 |
| 2009/0192384 A1 | 7/2009 | Fontius | |
| 2009/0299175 A1 * | 12/2009 | Bernstein et al. ............ | 600/425 |
| 2010/0109848 A1 * | 5/2010 | Blair et al. ................... | 340/10.2 |
| 2010/0152600 A1 * | 6/2010 | Droitcour et al. ............ | 600/534 |
| 2011/0004276 A1 * | 1/2011 | Blair et al. ...................... | 607/60 |

FOREIGN PATENT DOCUMENTS

DE  10 2006 036 575 A1  2/2008
EP  2 040 336 A1  7/2008

* cited by examiner

*Primary Examiner* — Baisakhi Roy
(74) *Attorney, Agent, or Firm* — Schiff Hardin LLP

(57) ABSTRACT

A patient bed for an imaging medical apparatus has a patient support plate that has at least one radar antenna to obtain physiological and/or geometric data from a patient the patient support plate. In a method for the operation of such a patient bed having at least one radar antenna in an imaging medical apparatus, the at least one radar antenna is operated to obtain data from the patient on the patient support plate.

35 Claims, 2 Drawing Sheets

RADAR-EQUIPPED PATIENT BED FOR A MEDICAL IMAGING APPARATUS, AND OPERATING METHOD THEREFOR

BACKGROUND OF THE INVENTION

1. Field of the Invention

The invention concerns a patient bed, in particular equipment of a patient support plate of the patient bed with the capability to acquire information about a patient on the patient support plate or the patient bed, and a method to operate the patient bed. The invention moreover concerns an imaging medical apparatus which possesses such a patient bed.

2. Description of the Prior Art

Imaging medical apparatuses—in particular larger imaging medical apparatuses such as magnetic resonance apparatuses, x-ray computed tomography systems for slice imaging, and x-ray systems having a larger C-arm x-ray apparatus—normally have a patient bed for supporting a patient during the imaging. Such patient beds are at times equipped with different types of devices, for example in order to obtain information about the position of a patient on the patient bed in the operation of the imaging apparatus. For example, in DE 10 2006 036 575 A1 a patient bed provided for computed tomography is described that has x-ray-positive markings to determine the position of the patient in diagnostic use of the computed tomography.

SUMMARY OF THE INVENTION

An object of the present invention is to provide a patient bed, a method for operating the patient bed and an imaging medical apparatus of the aforementioned type such that information about a patient borne on the patient bed can be obtained.

According to the invention, this object is achieved by a patient bed for an imaging medical apparatus with a support plate that has (carries) at least one radar antenna. The invention is based on the insight that, with radar technology, it is possible to determine not only geometric data and information concerning the position and alignment of a patient on the patient support plate but also to determine physiological data or parameters of a patient on the patient support plate, for example concerning breathing and heart rate. Primary signals in the form of electromagnetic waves are emitted in the direction of the patient with the at least one radar antenna. If the patient support plate has only one radar antenna, the secondary signals reflected by the patient or tissues of the patient are received with the same radar antenna and supplied to a control and evaluation unit for analysis. If the patient support plate has multiple radar antennas, each of the radar antennas can emit primary signals in the direction of the patient. The secondary signals can be received by one or by multiple radar antennas and be supplied to the control and evaluation unit.

By providing the at least one radar antenna in or on the patient support plate, the radar antenna moves with the patient as well upon displacements of the patient support plate (for example relative to an image acquisition system) so that there are no relative movements between the patient and the at least one radar antenna. This simplifies the evaluation of the secondary signals received with the radar antenna, in particular the extraction of the desired geometric and/or physiological data or, respectively, parameters from the secondary coils.

The provision of the at least one radar antenna in or on the patient support plate additionally has the advantage that the distance between patient and radar antenna is minimized in practice, such that the effect of the environment of the patient bed on the radar signals is relatively small.

According to one variant of the invention, the at least one radar antenna is a type of antenna known as a patch antenna. For example, a patch antenna has a quadratic or rectangular metal surface or metal layer whose longitudinal side advantageously exhibits a length of $\lambda/2$, ($\lambda$ being the employed wavelength) such that the metal surface acts as a resonator. In the case of the present invention, a patch antenna is very well suited as a radar antenna since it can be realized very flat and thus can easily be provided in the patient support plate.

The layer thickness of the metal surface of a patch antenna advantageously lies between 2 μm and 20 μm, preferably at 5 μm. The layer thickness of the metal surface is normally on the order of the skin depth of the metal, which is dependent on the operating frequency or, respectively, operating frequencies that is/are used. For example, copper has a skin depth of 6.6 μm at a frequency of 100 MHz. Therefore, in this case layer thicknesses above approximately 10 μm only negligibly improve the function of the patch antenna. At higher frequencies the skin depth (and therefore the necessary layer thickness of the patch antenna) is further reduced. The minimization of the layer thickness of the patch antenna is in particular applied if the metal layer should be exposed by x-rays (for example in computed tomography apparatuses or C-arm apparatuses) in order to minimize the x-ray absorption of the metal layer.

As mentioned, the patch antenna or the metal layer of the patch antenna can be executed as a square or rectangle. However, the patch antenna can have a different shape, in particular a shape adapted to the directional characteristic to be achieved with the patch antenna. The dimensions of a patch antenna are primarily conformed to its desired operating frequency, which in the case of the present invention is preferably between 100 MHz and 5 GHz.

An additional variant of the invention provides that the patient support plate has an array of radar antennas, in particular an array of patch antennas. At least two radar antennas are preferably arranged next to one another. The array of adjacently arranged radar antennas advantageously covers the entire surface of the patient support plate except for the required interstices between the radar antennas, such that every body part or the entire body of a patient on the patient support plate can be detected with the array.

Providing an array of radar antennas additionally affords the possibility to select from the array of radar antennas that radar antenna, or a pair or pairs of transmission and reception antennas, which deliver(s) the signal or signals that is/are best suitable to determine geometric and/or physiological data or, respectively, parameters.

In addition to a simple antenna selection, the correlation of the signals of multiple antennas can also be used to obtain information.

According to one embodiment of the invention, the patient bed or, respectively, the patient support plate of the patient bed has an (advantageously flexible) film or an (advantageously rigid) substrate layer that caries or embodies the at least one radar antenna. The radar antenna or the array of radar antennas is preferably arranged on the side of the film or the substrate layer facing toward the patient. If the radar antennas are patch antennas, these are arranged in rows and columns or like a matrix on the side of the film or substrate layer facing towards the patient, for example.

According to one embodiment of the invention, the film or the substrate layer is fashioned from a material for circuit boards. For example, the material can be FR4 (epoxy resin and glass cloth). Alternatively, a flexible polyimide film is considered.

According to a further embodiment of the invention, the film or the substrate layer has at least one electrically conductive coating in addition to the radar antenna or the array of radar antennas. The film or the substrate layer can also have multiple layers of electrically conductive coatings. Such an electrically conductive coating is advantageously fashioned flat and is integrated on the side of the film facing away from the patient. This electrically conductive coating serves as a reflector, so a directional effect or a directional characteristic toward the patient results for the radar antenna or the array of radar antennas.

The patient support plate itself can serve as a reflector if it is produced from a conductive material (for example carbon fiber).

According to one variant of the invention, the at least one electrically conductive coating is a metallic coating, for example a coating made of copper. The thickness of the coating is normally between 2 μm and 20 μm, advantageously at 5 μm.

The thin layer thicknesses of the patch antennas and the reflector layer are in particular advantageous if the patient bed is generally provided for an x-ray computed tomography or an x-ray apparatus, since the patch antennas and the reflector layer cause only slight image artifacts (if at all) when they are located in the beam path of the x-ray radiation.

If multiple layers of electrically conductive coatings are used, these can serve to construct a stacked patch antenna, for example. Alternatively or simultaneously, striplines for the antenna(a) can be realized with multiple electrically conductive layers. Such a stripline can, for example, be designed such that the actual electrical conductor is located between two electrically conductive coatings serving as grounds, these two electrically conductive coatings reducing the influence of interference signals. The striplines that are realized in this way are normally located outside of the area or the array of the patch antennas, meaning that the additional stacked, metallic coatings that are used for the striplines are normally not continuous over the entire film or the entire substrate layer. The striplines are preferably located in the border region of the film or the substrate layer.

According to one variant of the invention, the film or the substrate layer has a thickness between 0.5 mm and 2.5 mm and can therefore simply be incorporated into the patient support plate. The film or the substrate layer is advantageously completely integrated into the patient support plate, or the film or substrate layer is applied on the surface of the patient support plate facing towards the patient. In particular, a flexibly executed film is fitted in this manner to the surface of the patient support plate, which is typically not completely flat but rather exhibits curves. This also prevents, in the event that the patient bed is associated with an x-ray apparatus, the film from being exposed orthogonally in a specific position of the x-ray radiator, i.e. in the direction of its transverse extent, where the effective thickness of the film would be so large that significant image artifacts would occur.

In the design of a radar antenna it is advantageous to consider its use conditions. Among these are the curvature of the radar antenna if it is fitted to the surface of the patient support plate; the effect of the patient directly above the radar antenna; and the variation of this effect due to the anatomy of different patients. Furthermore, it is suggested to also take into account the variation of the antenna geometry that is caused by the pressure of the patient lying on the radar antenna.

The relative position of radar antenna and patient is such that the patient is normally located in the near field of the radar antenna. The design of the antenna field by itself thus should ensue so that the volume of interest of the patient can be specifically detected with the near field of the radar antenna, in particular in order to be able to observe physiological processes in the patient. Furthermore, the interference radiation and interference sensitivity of the radar antenna can be minimized by a minimization of the power radiated in the far field or received from the far field.

According to one embodiment of the invention, the patient bed has a base or a stand on which the patient support plate is arranged such that it can advantageously be moved, and the control and evaluation unit that is required for operation of the at least one radar antenna and that is electrically connected with the at least one radar antenna is arranged in the base or in the stand. In this way, for example in the case of an x-ray apparatus, the control and evaluation unit always remains outside of the beam path of the x-ray radiation and can even be shielded against x-ray scatter radiation if needed.

The object of the invention is also achieved by a method for operating a patient bed as described in the preceding, having at least one radar antenna, in which the at least one radar antenna is operated using a pulse radar method (for example in the form of ultrabroadband radar (UWB radar)). Utilizing the properties of electromagnetic fields with a relatively large bandwidth, information about the state of an environment— or about a patient in the case of the present invention—can be acquired non-destructively, without contact and with a resolution that is also sufficient for medical applications with UWB radar.

According to a variant of the invention, a 3D image of a patient on the patient support plate is generated with this method, advantageously using an array of radar antennas.

According to an additional variant of the invention, with the method physiological parameters of a patient borne on the patient support plate, the position of a patient on the patient support plate and/or the alignment of a patient on the patient support plate is/are determined, which information can be used in the imaging with the imaging apparatus.

The object forming the basis of the invention is moreover achieved by an imaging medical apparatus having a patient bed as described in the preceding.

The imaging apparatus is advantageously an x-ray computed tomography apparatus, a C-arm x-ray apparatus or an ultrasound apparatus.

DESCRIPTION OF THE PREFERRED EMBODIMENTS

Figure 1:
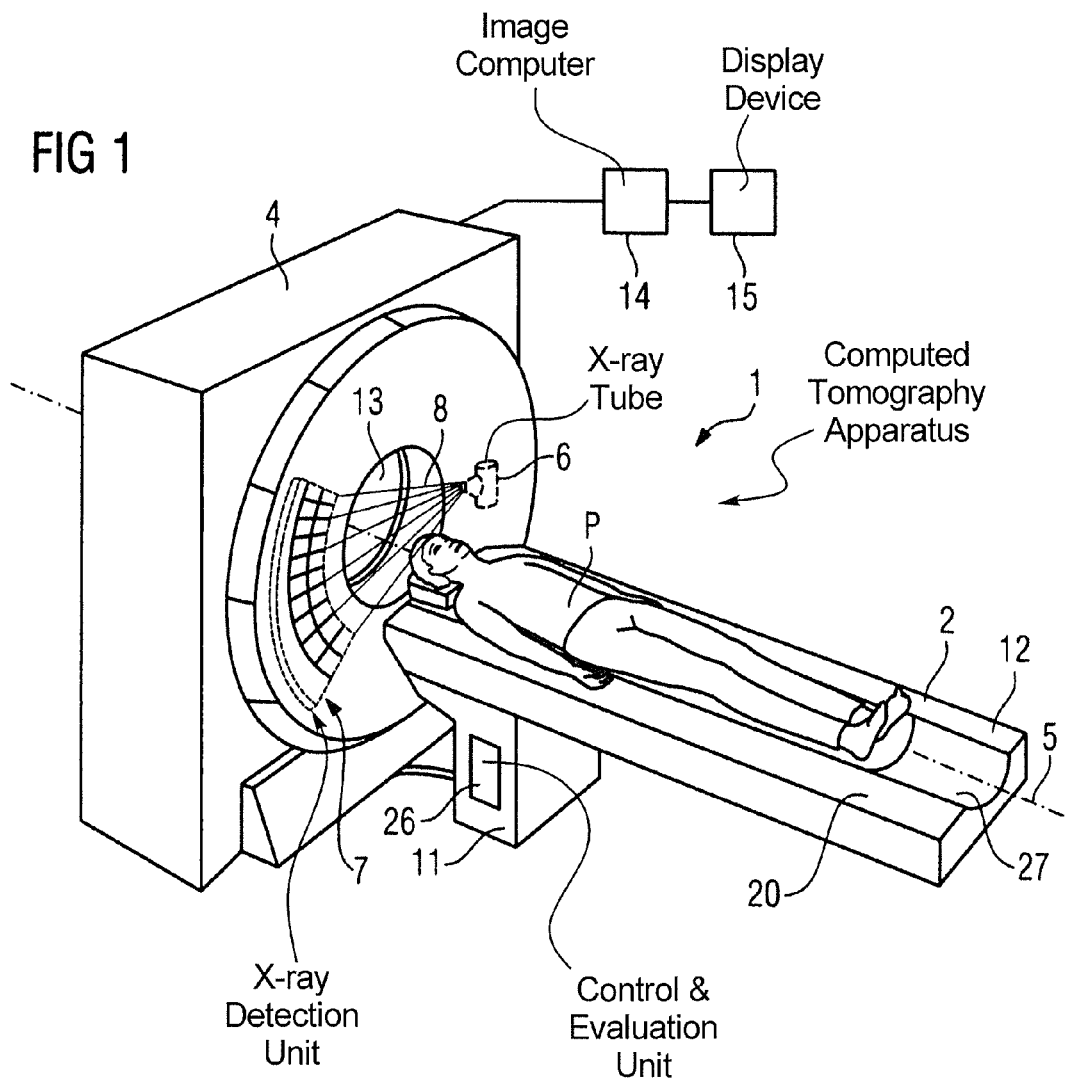
FIG. 1 shows an x-ray computed tomography with a patient bed.

Identical or functionally identical elements in the Figures are consistently provided with identical reference characters. The depictions in the Figures are schematic and not necessarily to scale, wherein scales can vary between the Figures. In the following the x-ray computed tomography apparatus and the patient bed of the x-ray computed tomography apparatus are discussed only generally and without limitation of generality, insofar as it is deemed necessary to understand the invention.

An x-ray computed tomography apparatus 1 with a patient bed 2 to support a patient P to be examined is shown in FIG. 1. The x-ray computed tomography apparatus 1 also has a gantry 4 with a CT data acquisition system mounted therein such that it can rotate around a system axis 5. The CT data acquisition system includes an x-ray tube 6 and an x-ray detector unit 7 opposite one another. In operation, x-ray radiation 8 emanates from the x-ray tube in the direction of the x-ray detector unit 7 and is detected therewith.

In the present exemplary embodiment of the invention, the patient bed 2 has a base or a stand 11 on which is arranged a patient support plate 12, provided to actually support the patient P. The patient support plate 12 is adjustable relative to the stand 11 such that the patient support plate 12 with the patient P can be inserted into the opening 13 of the gantry 4 to acquire 2D x-ray projections of the patient P (for example in a spiral scan). The computational processing of the 2D x-ray images or the reconstruction of slice images or 3D images based on the 2D x-ray projections ensues with an image computer 14 (schematically shown) of the x-ray computed tomography apparatus 1, which slices images or 3D images can be shown on a display device 15.

Figure 2:
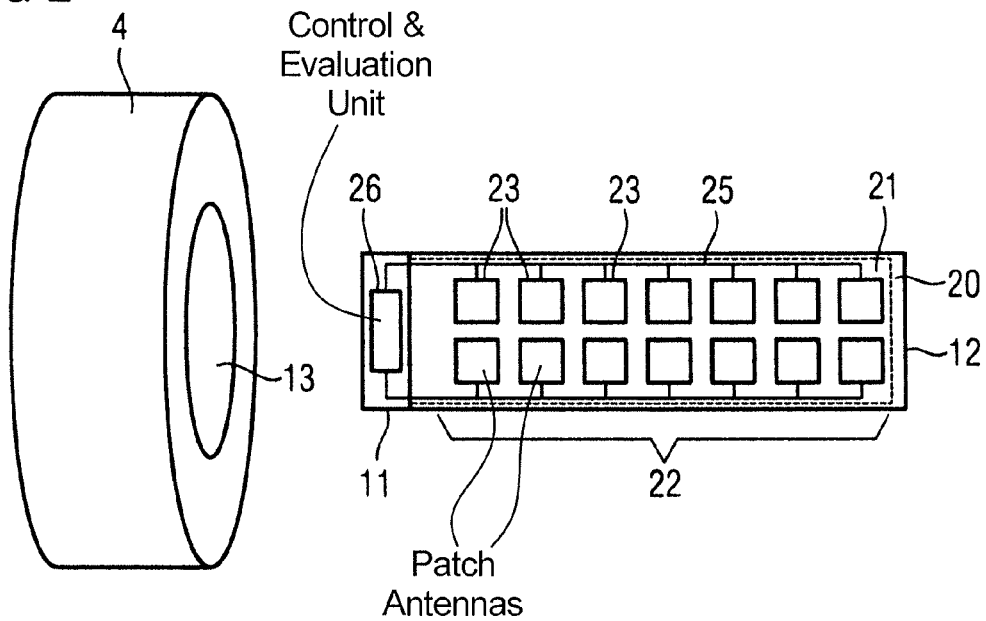
FIG. 2 is a simplified depiction of the patient bed of FIG. 1, provided with a film.

To explain the present invention, the patient bed 2 (in particular the patient support plate 12 of the patient bed 2) is shown in a simplified plan view in FIG. 2.

In the exemplary embodiment of the invention, the surface 20 of the patient support plate 12 that is facing toward the patient P is provided with a flexible film 21 that possesses an array 22 of radar antennas 23.

The film 21 exhibits a thickness between 0.5 mm and 2.5 mm (advantageously of approximately 1 mm) and is fashioned from a material for circuit boards, at present from polyimide.

Figure 3:
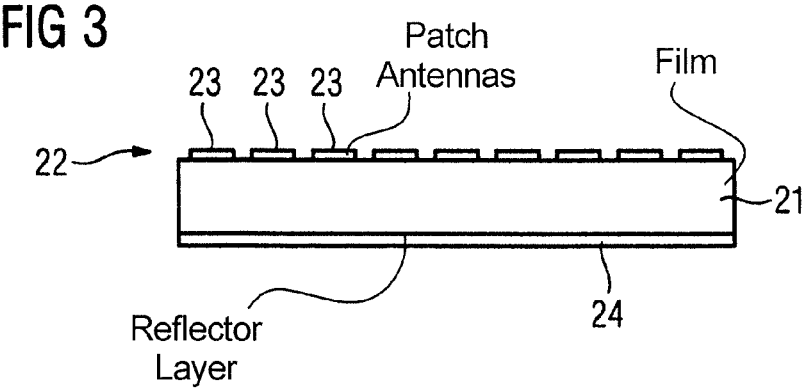
FIG. 3 shows the film from FIG. 2 in a simplified side view.

In the exemplary embodiment of the invention, the film 21 is provided with an electrically conductive metallic coating 24 on its side facing toward the surface 20 of the patient support plate 12, as this is apparent from FIG. 3. The metallic coating 24 is advantageously laminar, i.e. executed continuously. The metallic coating can, for example, be a coating of copper that possesses a thickness between 2 μm and 20 μm, advantageously of approximately 10 μm. The metallic coating serves as a shield or reflector; a directional effect or directional characteristic is thereby achieved so that the propagation of the radar waves is essentially limited to the side of the film 21 on which the patient P is located.

As is apparent from FIG. 2 and FIG. 3, in the exemplary embodiment of the invention the radar antennas of the array 22 are realized as patch antennas 23. Each patch antenna 23 of the array 22 in the present case has a quadratic metal surface which acts as a resonator. Each metal surface or metal layer can be a copper surface or, respectively, a copper layer that possesses a layer thickness between 2 μm and 20 μm, advantageously of approximately 10 μm. The metal surfaces of the patch antennas 23 do not necessarily have to be quadratic surfaces. Rather, the metal surfaces can also be rectangular or executed in different shapes, insofar as may be reasonable. The patch antennas 23 are preferably arranged or located on the side of the film 21 facing toward the patient so that optimally the entire body of a patient P who is supported on the patient support plate 12 or the film 21 can be charged with radar signals.

The film 21 is advantageously arranged resting flat on the surface 20, in particular on the curved part 27 of the surface 20 of the patient support plate 12. For this purpose, the film 21 can be glued to the surface 20 of the patient support plate 12, for example.

The patch antennas 23 of the array 22 are electrically connected with an electronic radar unit (in the form of a control and evaluation unit 26) via conductors 25 which can be striplines on the film 21. In the case of the present exemplary embodiment of the invention, the control and evaluation unit 26 is integrated into the stand 11 and is accordingly always located outside of the beam path of the x-ray radiation 8. The control and evaluation unit 26 can additionally be shielded against x-ray scatter radiation in a manner that is not shown, for example with a plate or a housing made of lead. The control and evaluation unit 26 is moreover connected with the image computer 14 for data exchange.

In the exemplary embodiment of the invention, the array 22 of patch antennas 23 is preferably operated using a pulse radar method—in particular ultrabroadband radar (UWB radar)—with the control and evaluation unit 26. Geometric and physiological information, data or parameters about the state of the patient P borne on the patient support plate 12 or on the film 21 can be obtained with UWB radar. For this purpose. electromagnetic primary signals are emitted with the patch antenna and electromagnetic secondary signals reflected on body tissue of the patient P (that are in turn evaluated or, respectively, analyzed by the control and evaluation unit 26) are received, controlled by said control and evaluation unit 26 (which is normally a computer).

A rather rough (in terms of the resolution) 3D image of the patient is preferably determined with the control and evaluation unit 26, based on the secondary signals received with the patch antennas 23. However, the 3D image is sufficient in order to be able to determine the position and the alignment of the patient P on the patient support plate 12. The 3D image can be shown on the display device 15. Furthermore, the 3D image can simultaneously or alternatively be input into the acquisition planning and/or control functions of the x-ray computed tomography apparatus 1.

Moreover, physiological information, data or, respectively, parameters of the patient P can also be determined using the 3D image and using the continuous or intermittent operation of the array 22 of patch antennas 23. The possibility thus exists to determine the breathing cycle of the patient from the detection and evaluation of the secondary signals reflected by the moving rib cage of the patient P. The cardiac cycle of the patient can be determined in a comparable manner from the detection and evaluation of the secondary signals reflected by the moving heart of the patient P. Moreover, not all patch antennas 23 of the array 22 must be continuously operated for this purpose. Rather, the patch antenna 23 or the patch antennas 23 of the array 22 can initially be identified whose received secondary signals are best suited to determine the breathing cycle or to determine the cardiac cycle. Only this identified patch antenna 23 or these identified patch antennas 23 can subsequently be operated to determine the breathing or cardiac cycle.

The geometric and/or physiological data that is obtained in this way can be shown on the display device 15 and also be used in the data (image) acquisition planning for the x-ray computed tomography apparatus 1, for example as input parameters for the dose modulation depending on the radiation direction; or, in a scan of the heart, the point in time of the acquisition of a 2D projection can be established based on the determined cardiac cycle.

The film 21 carrying the array 22 of patch antennas 23 can be retrofitted in a simple manner to existing patient beds or medical imaging apparatuses.

The array 22 of patch antennas 23 and the metallic reflector layer 24 do not necessarily have to possess a flexible film as a substrate. Alternatively, a different substrate—in particular a rigid substrate or a rigid substrate layer—can also be provided that has the array of patch antennas on one side and a metallic reflector layer on its other side. Both the film 21 and another substrate possessing the array of patch antennas and the metallic reflector layer can be completely integrated (in the sense of accommodated, in particular accommodated such that they cannot be externally detected) into the patient support plate or the patient bed. In this sense a patient substrate that can be placed on an adjustable patient board is also understood as a patient support plate.

In contrast to the described exemplary embodiment of the invention, the patient support plate can also be fashioned so as to be completely flat, such that the film or substrate layer is also executed flat to match the patient support plate.

Furthermore, the radar antenna does not necessarily need to be a patch antenna. Rather, other suitable radar antennas can also be provided in or on the patient support plate.

The imaging apparatus can also be a C-arm x-ray apparatus or an ultrasound apparatus.

Although modifications and changes may be suggested by those skilled in the art, it is the intention of the inventors to embody within the patent warranted hereon all changes and modifications as reasonably and properly come within the scope of their contribution to the art.

We claim as our invention:

1. A patient bed for a medical imaging apparatus, comprising:
    a patient support plate configured to receive a patient thereon;
    at least one radar antenna mounted at said patient support plate and configured to operate at an operating frequency to radiate a primary signal to said patient on said patient support plate and to receive a secondary signal reflected from the patient on the patient support plate;
    said at least one radar antenna comprising a metal surface or metal layer having a thickness corresponding to a skin depth of the metal defined at said operating frequency; and
    a control and evaluation unit configured to operate said at least one radar antenna to radiate said primary signal and to receive said secondary signal, and configured to generate, from said secondary signal, at least one of physiological data and geometric data from the patient on the patient support plate.

2. A patient bed as claimed in claim 1 wherein said at least one radar antenna is a patch antenna.

3. A patient bed as claimed in claim 2 wherein said patch antenna has a layer thickness in a range between 2 μm and 20 μm.

4. A patient bed as claimed in claim 1 comprising a radar antenna array mounted at said patient support plate.

5. A patient bed as claimed in claim 1 comprising at least two radar antennas mounted at said patient support plate that are located adjacent to each other.

6. A patient bed as claimed in claim 1 wherein said patient support plate comprises a flat patient support plate component, selected from the group consisting of a film and a substrate layer, at which said at least one radar antenna is mounted.

7. A patient bed as claimed in claim 6 wherein said patient support plate component is comprised of circuit board material.

8. A patient bed as claimed in claim 6 wherein said patient support plate component comprises at least one electrically conductive coating, in addition to said at least one radar antenna.

9. A patient bed as claimed in claim 8 wherein said electrically conductive coating is a continuous coating on a side of said patient support plate component facing away from the patient.

10. A patient bed as claimed in claim 8 wherein said electrically conductive coating is a metallic coating.

11. A patient bed as claimed in claim 8 wherein said electrically conductive coating has a thickness in a range between 2 μm and 20 μm.

12. A patient bed as claimed in claim 6 wherein said patient support plate component has a thickness in a range between 0.5 mm and 2.5 mm.

13. A patient bed as claimed in claim 6 wherein said patient support plate component is integrated into said patient support plate.

14. A patient bed as claimed in claim 6 wherein said patient support plate component is applied at a side of said patient support plate facing toward the patient.

15. A patient bed as claimed in claim 1 comprising a base on which said patient support plate is mounted, and wherein said control and evaluation unit is located in said base.

16. A method for operating a patient bed of a medical imaging apparatus, comprising the steps of:
    placing a patient on a patient support plate in a medical imaging apparatus;
    embodying at least one radar antenna in said patient support plate; and
    operating said at least one radar antenna in said patient support plate at an operating frequency to radiate a primary signal to the patient on the patient support plate and to receive a secondary signal reflected from the patient;
    configuring said at least one radar antenna to have a metal surface or metal layer having a thickness corresponding to a skin depth of the metal defined at said operating frequency; and
    in a processor, generating, from said secondary signal, at least one of physiological data and geometric data from the patient.

17. A method as claimed in claim 16 comprising operating said at least one radar antenna in a pulsed radar mode.

18. A method as claimed in claim 16 comprising generating a 3D image of the patient on the patient support plate from data obtained from the patient with said at least one radar antenna.

19. A method as claimed in claim 16 comprising acquiring geometric data from the patient on the patient support plate with said at least one radar antenna, and electronically evaluating said geometric data to determine at least one of a position of the patient on the patient support plate and an alignment of the patient on the patient support plate relative to the medical imaging apparatus.

20. A method as claimed in claim 16 comprising acquiring physiological data from the patient on the patient support plate, and evaluating said physiological data to determine at least one of a respiration cycle and a cardiac cycle of the patient on the patient support plate.

21. A medical imaging apparatus comprising:
    a data acquisition unit configured to acquire medical image data from a patient therein;
    a patient support plate configured to support a patient in the data acquisition unit on the patient support plate;
    at least one radar antenna mounted at said patient support plate configured to radiate a primary signal to the patient on the patient support plate and to receive a secondary signal reflected from the patient on the support plate; and
    a control and evaluation unit configured to operate said at least one radar antenna at an operating frequency to radiate said primary signal and to detect said secondary signal and to evaluate said secondary signal to determine at least one of geometric data and physiological data from the patient on the patient support plate; and said at least one radar antenna comprising a metal surface or metal layer having a thickness corresponding to a skin depth of the metal defined at said operating frequency.

22. A medical imaging apparatus as claimed in claim 21 wherein said data acquisition unit is selected from the group consisting of an x-ray computed tomography apparatus, a C-arm x-ray apparatus, and an ultrasound apparatus.

23. A patient bed for a medical imaging apparatus, comprising:
  a patient support plate configured to receive a patient thereon;
  at least one radar antenna mounted at said patient support plate and configured to radiate a primary signal to said patient on said patient support plate and to receive a secondary signal reflected from the patient on the patient support plate;
  said at least one radar antenna comprising a metal surface or metal layer having a thickness corresponding to a skin depth of the metal defined at said operating frequency; and
  a control and evaluation unit configured to operate said at least one radar antenna with an ultra-wideband operating method to radiate said primary signal and to receive said secondary signal, and configured to generate, from said secondary signal, at least one of physiological data and geometric data from the patient on the patient support plate.

24. A patient bed for a medical imaging apparatus, comprising:
  a patient support plate configured to receive a patient thereon;
  at least one radar antenna mounted at said patient support plate and configured to radiate a primary signal to said patient on said patient support plate and to receive a secondary signal reflected from the patient on the patient support plate;
  said at least one radar antenna comprising a metal surface or metal layer having a thickness corresponding to a skin depth of the metal defined at said operating frequency;
  a control and evaluation unit configured to operate said at least one radar antenna to radiate said primary signal and to receive said secondary signal, and configured to generate, from said secondary signal, at least one of physiological data and geometric data from the patient on the patient support plate; and
  a computer configured to generate a 3D image of the patient from the secondary signals.

25. A method for operating a patient bed of an x-ray computed tomography (CT) apparatus, comprising the steps of:
  placing a patient on a patient support plate in an x-ray CT apparatus;
  embodying at least one radar antenna in said patient support plate;
  operating said at least one radar antenna in said patient support plate with an ultra-wideband operating method to radiate a primary signal to the patient on the patient support plate and to receive a secondary signal reflected from the patient;
  in a processor, generating, from said secondary signal, at least one of physiological data and geometric data from the patient; and
  for obtaining an image of the heart of the patient, in a procedure using said x-ray CT apparatus, claiming or executing said procedure by setting a parameter of said procedure dependent on at least one of said physiological data and said geometric data, and selecting said parameter from the group consisting of a dose modulation that is dependent on a direction of irradiation of the heart with x-rays emitted by said x-ray CT apparatus, and a point in time of acquisition of a 2D projection of the heart would then be cardiac cycle of the patient.

26. A method for operating a patient bed of a medical imaging apparatus, comprising the steps of:
  placing a patient on a patient support plate in an x-ray CT apparatus;
  embodying at least one radar antenna in said patient support plate; and
  operating said at least one radar antenna in said patient support plate to radiate a primary signal to the patient on the patient support plate and to receive a secondary signal reflected from the patient;
  in a processor, generating, from said secondary signal, at least one of physiological data and geometric data from the patient;
  in a computer, generating a 3D image of the patient from the secondary signal; and
  for obtaining an image of the heart of the patient, in a procedure using said x-ray CT apparatus, claiming or executing said procedure by setting a parameter of said procedure dependent on said 3D image, and selecting said parameter from the group consisting of a dose modulation that is dependent on a direction of irradiation of the heart with x-rays emitted by said x-ray CT apparatus, and a point in time of acquisition of a 2D projection of the heart would then be cardiac cycle of the patient.

27. A medical imaging apparatus comprising:
  a data acquisition unit configured to acquire medical image data from a patient therein;
  a patient support plate configured to support a patient in the data acquisition unit on the patient support plate;
  at least one radar antenna mounted at said patient support plate configured to radiate a primary signal to the patient on the patient support plate and to receive a secondary signal reflected from the patient on the support plate;
  said at least one radar antenna comprising a metal surface or metal layer having a thickness corresponding to a skin depth of the metal defined at said operating frequency; and
  a control and evaluation unit configured to operate said at least one radar antenna with an ultra-wideband operating method to radiate said primary signal and to detect said secondary signal and to evaluate said secondary signal to determine at least one of geometric data and physiological data from the patient on the patient support plate.

28. A medical imaging apparatus comprising:
  a data acquisition unit configured to acquire medical image data from a patient therein;
  a patient support plate configured to support a patient in the data acquisition unit on the patient support plate;
  at least one radar antenna mounted at said patient support plate configured to radiate a primary signal to the patient on the patient support plate and to receive a secondary signal reflected from the patient on the support plate;
  said at least one radar antenna comprising a metal surface or metal layer having a thickness corresponding to a skin depth of the metal defined at said operating frequency;
  a control and evaluation unit configured to operate said at least one radar antenna to radiate said primary signal and to detect said secondary signal and to evaluate said secondary signal to determine at least one of geometric data and physiological data from the patient on the patient support plate; and a computer configured to generate a 3D image of the patient from the secondary signals.

29. A patient bed as claimed in claim 1, wherein said thickness of said metal surface or said metal layer has a value in a range that is within a decimal power of said skin depth at said operating frequency, and that does not exceed said skin depth at said operating frequency.

30. A method as claimed in claim 16, comprising configuring said thickness of said metal surface or said metal layer has a value in a range that is within a decimal power of said skin depth at said operating frequency, and that does not exceed said skin depth at said operating frequency.

31. A medical imaging apparatus as claimed in claim 21, wherein said thickness of said metal surface or said metal layer has a value in a range that is within a decimal power of said skin depth at said operating frequency, and that does not exceed said skin depth at said operating frequency.

32. A patient bed as claimed in claim 23, wherein said thickness of said metal surface or said metal layer has a value in a range that is within a decimal power of said skin depth at said operating frequency, and that does not exceed said skin depth at said operating frequency.

33. A patient bed as claimed in claim 24, wherein said thickness of said metal surface or said metal layer has a value in a range that is within a decimal power of said skin depth at said operating frequency, and that does not exceed said skin depth at said operating frequency.

34. A medical imaging apparatus as claimed in claim 27, wherein said thickness of said metal surface or said metal layer has a value in a range that is within a decimal power of said skin depth at said operating frequency, and that does not exceed said skin depth at said operating frequency.

35. A medical imaging apparatus as claimed in claim 28, wherein said thickness of said metal surface or said metal layer has a value in a range that is within a decimal power of said skin depth at said operating frequency, and that does not exceed said skin depth at said operating frequency.

* * * * *